US007871641B2

(12) United States Patent
Lau et al.

(10) Patent No.: US 7,871,641 B2
(45) **Date of Patent: *Jan. 18, 2011**

(54) HEPATOCYTE-TARGETING VEHICLE FOR DELIVERY OF GLARGINE INSULIN TO A MAMMAL

(75) Inventors: John R. Lau, Howard, OH (US); W. Blair Geho, Wooster, OH (US)

(73) Assignee: SDG, Inc., Wooster, OH (US)

( * ) Notice: Subject to any disclaimer, the term of this patent is extended or adjusted under 35 U.S.C. 154(b) by 1122 days.

This patent is subject to a terminal disclaimer.

(21) Appl. No.: 11/384,728

(22) Filed: Mar. 20, 2006

(65) Prior Publication Data

US 2006/0222698 A1 Oct. 5, 2006

Related U.S. Application Data

(63) Continuation-in-part of application No. 09/313,828, filed on May 18, 1999, now Pat. No. 7,169,410.

(60) Provisional application No. 60/085,969, filed on May 19, 1998.

(51) Int. Cl.
*A61K 9/127* (2006.01)

(52) U.S. Cl. ..................... 424/450; 424/78.08; 424/321

(58) Field of Classification Search ....................... None
See application file for complete search history.

(56) References Cited

U.S. PATENT DOCUMENTS 4,603,044 A 7/1986 Geho et al.
4,963,526 A * 10/1990 Ecanow ......................... 514/3

FOREIGN PATENT DOCUMENTS

WO WO 88/00474 * 1/1988
WO WO 99/59545 (A1) 11/1999

OTHER PUBLICATIONS

Heinemann et al., Diabetes Care 23: 644-649, 2000.*

* cited by examiner

*Primary Examiner*—Robert Landsman
*Assistant Examiner*—Gyan Chandra
(74) *Attorney, Agent, or Firm*—Riverside Law, LLP

(57) ABSTRACT

The instant invention is drawn to a hepatocyte targeted composition comprising a mixture of free glargine insulin and glargine insulin associated with a water insoluble target molecule complex, wherein the complex comprises multiple linked individual units and a supra-molecular lipid construct matrix. Glargine insulin is present within the complex in at least one form wherein the glargine insulin has a positive charge which interacts with a negative charge on the complex. The invention also includes methods for the manufacture of the composition and methods of managing blood glucose levels in individuals with Type I and Type II diabetes.

14 Claims, 6 Drawing Sheets

Figure 3.

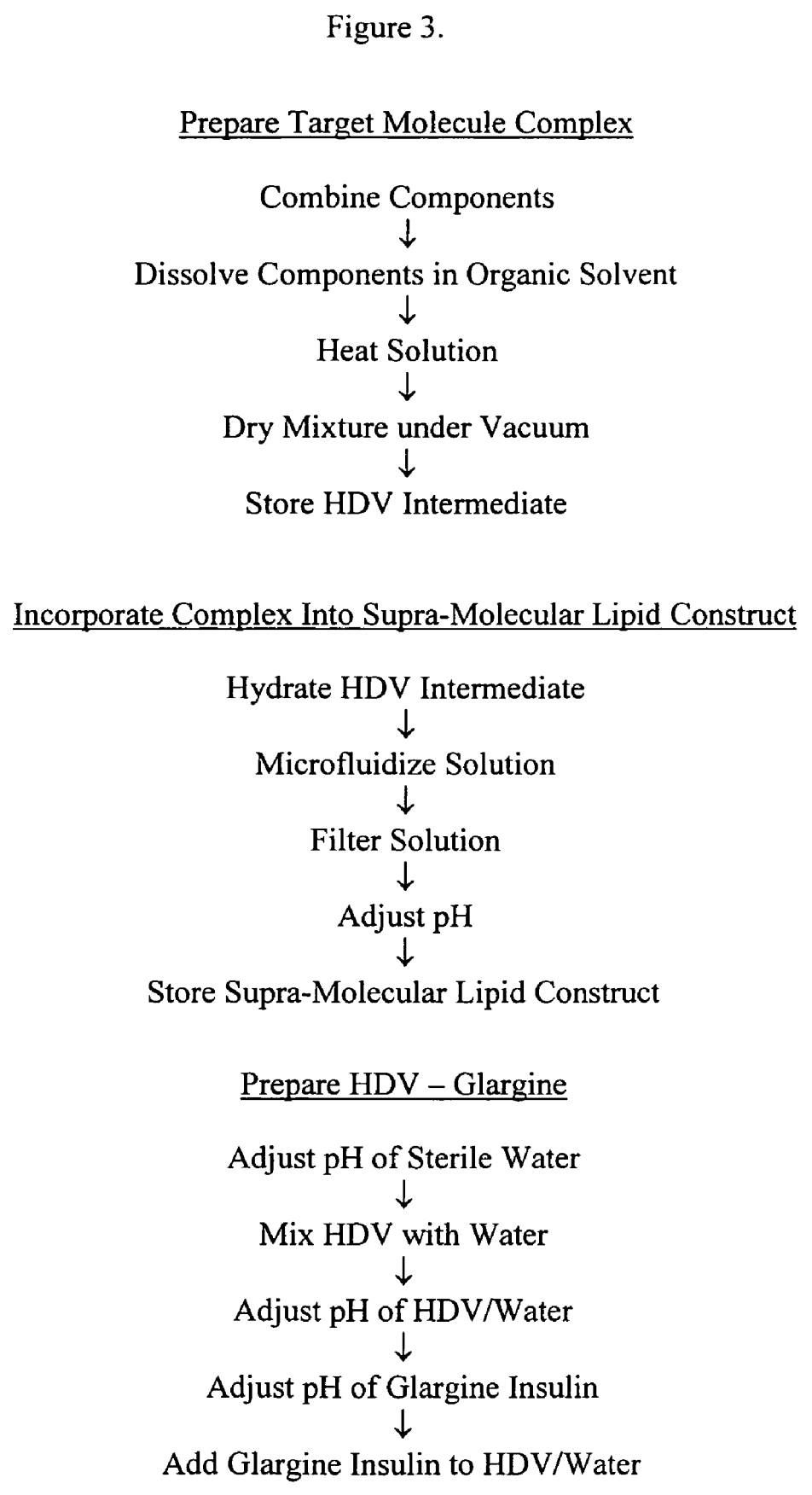

Prepare Target Molecule Complex

Combine Components
↓
Dissolve Components in Organic Solvent
↓
Heat Solution
↓
Dry Mixture under Vacuum
↓
Store HDV Intermediate Incorporate Complex Into Supra-Molecular Lipid Construct Hydrate HDV Intermediate
↓
Microfluidize Solution
↓
Filter Solution
↓
Adjust pH
↓
Store Supra-Molecular Lipid Construct Prepare HDV – Glargine Adjust pH of Sterile Water
↓
Mix HDV with Water
↓
Adjust pH of HDV/Water
↓
Adjust pH of Glargine Insulin
↓
Add Glargine Insulin to HDV/Water

HEPATOCYTE-TARGETING VEHICLE FOR DELIVERY OF GLARGINE INSULIN TO A MAMMAL

CROSS-REFERENCE TO RELATED APPLICATIONS

This application is a continuation-in-part of U.S. patent application Ser. No. 09/313,828, filed May 18, 1999, which claims priority to U.S. Provisional Patent Application No. 60/085,969, filed May 19, 1998, each of which is incorporated by reference herein in its entirety.

BACKGROUND OF THE INVENTION

Diabetes is a disorder affecting large numbers of people worldwide. Management approaches to control Type I and Type II diabetes aim primarily at normalizing blood glucose levels to prevent short- and long-term complications. Many patients require multiple daily injections of an insulin to control their diabetes. Several insulin products have been produced that control blood sugar levels over differing time intervals. Several products combine various forms of insulin in an attempt to provide a preparation which controls glucose levels over a wider period of time.

Previous attempts to normalize blood glucose levels in Type I and Type II diabetic patients have centered on the subcutaneous administration of insulin in various time-released formulations, such as Itralente and humulin NPH insulin pharmaceutical products. These formulations have attempted to delay and subsequently control the bio-distribution of insulin by regulating release of insulin to peripheral tissues with the expectation that sustained management of insulin bio-availability will lead to better glucose control. Glargine insulin is a long-acting form of insulin in which insulin is released from the subcutaneous tissue around the site of injection into the bloodstream at a relatively constant rate throughout the day. Although glargine insulin is released at a constant rate throughout the day, the released insulin reaches a wide range of systems within the body rather than being delivered to targeted areas of the body. What is needed is a composition of insulin where a portion of the dosed insulin is released at a relatively constant rate throughout the day and another portion of insulin that is time released from the site of administration and targeted for delivery to the liver to better control glucose production.

There is, therefore, an unmet need in the art for compositions and methods of managing blood glucose levels in Type I and Type II diabetic patients. The present invention meets these needs by providing a long-acting composition comprising glargine insulin that is free and glargine insulin that is associated with a supra-molecular lipid construct targeted for delivery to hepatocytes. A supra-molecular lipid construct is a lipid/phospholipid particle in which individual lipid molecules cooperatively interact to create a bipolar lipid membrane which encloses and isolates a portion of the medium in which it was formed. The supra-molecular lipid construct releases free glargine over time as well as targets a portion of the remaining glargine insulin to the hepatocytes in the liver to better control glucose storage and production.

BRIEF SUMMARY OF THE INVENTION

In one aspect, the present invention includes a hepatocyte-targeting composition comprising: free glargine insulin and glargine insulin associated with a water-insoluble target molecule complex; wherein the target molecule complex is comprised of a combination of: multiple linked individual units, the individual units comprising: at least one bridging component selected from the group consisting of a transition element, an inner transition element, and a neighbor element of the transition element; and a complexing component; and a supra-molecular lipid construct matrix comprising at least one lipid component; provided that when the transition element is chromium, a chromium target molecule complex is created; wherein the target molecule complex comprises a negative charge.

In another aspect, the composition further comprises at least one free non-glargine insulin and at least one non-glargine insulin associated with a water-insoluble target molecule complex.

In yet another aspect, non-glargine insulin is selected from the group consisting of lispro insulin, aspart insulin, regular insulin, lente insulin, ultralente insulin, recombinant human regular insulin, recombinant human insulin isophane or premixed combinations of any of the aforementioned insulins, and a combination of two or more of the aforementioned insulins.

In yet another aspect, non-glargine insulin comprises insulin-like moieties, including fragments of insulin molecules, that have the biological activity of insulins.

In still another aspect, the lipid component comprises at least one lipid selected from the group consisting of 1,2-distearoyl-sn-glycero-3-phosphocholine, 1,2-dipalmitoyl-sn-glycero-3-phosphocholine, 1,2-dimyristoyl-sn-glycero-3-phosphocholine, cholesterol, cholesterol oleate, dicetylphosphate, 1,2-distearoyl-sn-glycero-3-phosphate, 1,2-dipalmitoyl-sn-glycero-3-phosphate, and 1,2-dimyristoyl-sn-glycero-3-phosphate.

In yet another aspect, the lipid component comprises at least one lipid selected from the group consisting of 1,2-distearoyl-sn-glycero-3-phosphocholine, cholesterol, and dicetyl phosphate.

In one aspect, the lipid component comprises a mixture of 1,2-distearoyl-sn-glycero-3-phosphocholine, cholesterol and dicetyl phosphate.

In another aspect, the bridging component is chromium.

In still another aspect, the complexing component comprises at least one member selected from the group consisting of:

N-(2,6-diisopropylphenylcarbamoylmethyl)iminodiacetic acid;
N-(2,6-diethylphenylcarbamoylmethyl)iminodiacetic acid;
N-(2,6-dimethylphenylcarbamoylmethyl)iminodiacetic acid;
N-(4-isopropylphenylcarbamoylmethyl)iminodiacetic acid;
N-(4-butylphenylcarbamoylmethyl)iminodiacetic acid;
N-(2,3-dimethylphenylcarbamoylmethyl)iminodiacetic acid;
N-(2,4-dimethylphenylcarbamoylmethyl)iminodiacetic acid;
N-(2,5-dimethylphenylcarbamoylmethyl)iminodiacetic acid;
N-(3,4-dimethylphenylcarbamoylmethyl)iminodiacetic acid;
N-(3,5-dimethylphenylcarbamoylmethyl)iminodiacetic acid;
N-(3-butylphenylcarbamoylmethyl)iminodiacetic acid;
N-(2-butylphenylcarbamoylmethyl)iminodiacetic acid;
N-(4-tertiary butylphenylcarbamoylmethyl)iminodiacetic acid;
N-(3-butoxyphenylcarbamoylmethyl)iminodiacetic acid;
N-(2-hexyloxyphenylcarbamoylmethyl)iminodiacetic acid;
N-(4-hexyloxyphenylcarbamoylmethyl)iminodiacetic acid;

aminopyrrol iminodiacetic acid;

N-(3-bromo-2,4,6-trimethylphenylcarbamoylmethyl)iminodiacetic acid;

benzimidazole methyl iminodiacetic acid;

N-(3-cyano-4,5-dimethyl-2-pyrrylcarbamoylmethyl)iminodiacetic acid;

N-(3-cyano-4-methyl-5-benzyl-2-pyrrylcarbamoylmethyl) iminodiacetic acid; and

N-(3-cyano-4-methyl-2-pyrrylcarbamoylmethyl)iminodiacetic acid.

In yet another aspect, the complexing component comprises poly(bis)[N-(2,6-diisopropylphenylcarbamoylmethyl) iminodiacetic acid].

In one aspect, the present invention includes a method of manufacturing a hepatocyte targeted composition of the invention comprising: creating a target molecule complex, wherein the complex comprises multiple linked individual units and a supra-molecular lipid construct matrix; forming a suspension of the target molecule complex in water; adjusting the pH of the water suspension to approximately pH 5.3; adjusting the pH of glargine insulin to approximately pH 4.8; and combining glargine insulin and the target molecule complex.

In another aspect, a method of treating a patient for Type I or Type II diabetes comprises administering to the patient an effective amount of a hepatocyte targeted composition of the invention.

In still another aspect, the route of administration is selected from the group consisting of oral, parenteral, subcutaneous, pulmonary and buccal.

In yet another aspect, the route of administration is oral or subcutaneous.

In another aspect, the non-glargine insulin is selected from the group consisting of lispro insulin, aspart insulin, regular insulin, lente insulin, ultralente insulin, recombinant human regular insulin, recombinant human insulin isophane or premixed combinations of any of the aforementioned insulins, and a combination of two or more of the aforementioned insulins.

In still another aspect, a method of increasing the bioavailability of glargine insulin in a patient comprises: administering glargine insulin in a hepatocyte-targeting composition, the composition comprising free glargine insulin and glargine insulin associated with a water insoluble target molecule complex, wherein the complex comprises multiple linked individual units and a supra-molecular lipid construct matrix containing a negative charge, the multiple linked individual units comprising: (a) a bridging component selected from the group consisting of a transition element, an inner transition element, a neighbor element of the transition element and a mixture of any of the foregoing elements, (b) a complexing component, provided that when the transition element is chromium, a chromium target molecule complex is created, wherein the multiple linked individual units are combined with the supra-molecular lipid construct matrix, wherein the insulins are associated with the target molecule complex that contains a negative charge; thereby the association between glargine insulin and the water insoluble target molecule complex is altered within the patient to form new structures associated with the glargine insulin, wherein the new structures are present in soluble and insoluble forms and are delivered to sites of insulin activity.

In one aspect, the present invention comprises delivery of glargine insulin to fat, liver, and muscle.

In another aspect, delivery of glargine insulin to sites of insulin activity occurs over a plurality of meals.

In still another aspect, delivery of a hepatic component occurs at meal-time.

In yet another aspect, a kit for treating Type I or Type II diabetes in a mammal is provided, the kit comprising glargine insulin and a water insoluble target molecule complex, wherein the complex comprises multiple linked individual units and a supra-molecular lipid construct matrix containing a negative charge, the multiple linked individual units comprising: a bridging component selected from the group consisting of a transition element, an inner transition element, a neighbor element of the transition element and a mixture of any of the foregoing elements, and a complexing component, provided that when the transition element is chromium, a chromium target molecule complex is created, wherein the multiple linked individual units are combined with the supra-molecular lipid construct matrix, wherein the glargine insulin is associated with a target molecule complex, wherein said complex comprises a negative charge, the kit further comprising a physiological buffered solution, an applicator, and an instructional material for the use thereof.

In one aspect, a kit further comprises at least one non-glargine insulin.

BRIEF DESCRIPTION OF THE DRAWINGS

For the purposes of illustrating the invention, there is depicted in the drawings certain embodiments of the invention. However, the invention is not limited to the precise arrangements and instrumentalities of the embodiments depicted in the drawings.

FIG. 3 is an outline of the method of manufacturing a hepatocyte targeted pharmaceutical composition that combines free glargine insulin and glargine insulin associated with a water insoluble target molecule complex.

DETAILED DESCRIPTION OF THE INVENTION

Figure 1:
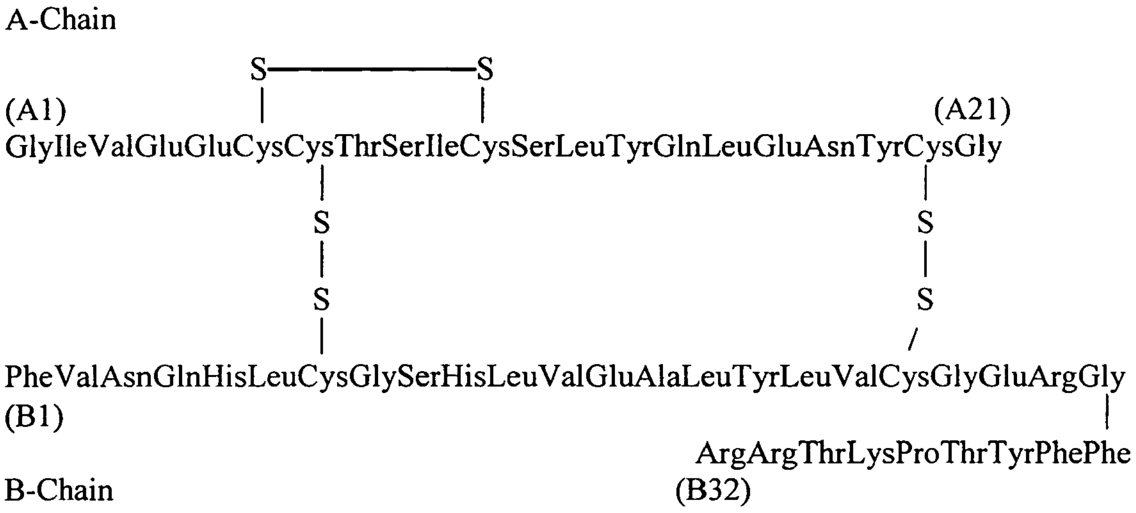
FIG. 1 is a depiction of the chemical structure of glargine insulin.

This invention includes a hepatocyte targeted pharmaceutical composition that combines free glargine insulin and glargine insulin associated with a water insoluble target molecule complex targeted to hepatocytes in the liver of a patient to provide an effective means of managing blood glucose levels. The composition can be administered subcutaneously or orally for the purpose of normalizing blood glucose levels in patients affected with abnormal glucose utilization.

The invention further provides a method of manufacturing a composition comprising free glargine insulin and glargine insulin associated with a water insoluble target molecule complex that targets delivery of the complex to the hepatocytes. The target molecule complex comprises a supra-molecular lipid construct matrix containing multiple linked individual units of a structure formed by a metal complex.

Additionally, the invention provides methods of managing blood glucose levels in individuals with Type I and Type II diabetes by administering an effective dose of a hepatocyte targeted pharmaceutical composition that combines free glargine insulin and glargine insulin associated with a water insoluble target molecule complex targeted for delivery to hepatocytes. The combination of free glargine insulin and glargine insulin associated with a water insoluble target molecule complex creates a dynamic equilibrium process between the two forms of insulin that occurs in vivo to help control the movement of free glargine insulin to the receptor sites of hormonal action, such as the muscle and adipose tissue of a diabetic patient over a designated time period. Hepatocyte targeted glargine insulin is also delivered to the liver of a diabetic patient over a different designated time period than free glargine insulin thereby introducing new pharmacodynamic profiles of insulin when free glargine insulin is released from the supra-molecular lipid construct. In addition, a portion of glargine insulin that is associated with the supra-molecular construct is targeted to the liver. This new pharmacodynamic profile of the product provides not only long-acting basal insulin for peripheral tissues, but also mealtime hepatic insulin stimulation for the management of hepatic glucose storage during a meal. Free glargine insulin is released from the site of administration and is distributed throughout the body. Glargine insulin associated with a water insoluble target molecule complex is delivered to the liver, where it is released over time from the complex. The rate of release of glargine insulin associated with the target molecule complex is different than the rate of release of free glargine insulin from the site of administration. These different release rates of insulin delivery, combined with the targeted delivery of insulin associated with a supra-molecular lipid construct to the liver, provide for the normalization of glucose concentrations in patients with Type I and Type II diabetes. The hepatocyte targeted composition can also comprise other types of insulin, or a combination of other types of insulin.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in organic chemistry and protein chemistry are those well known and commonly employed in the art.

The articles "a" and "an" are used herein to refer to one or to more than one (i.e., to at least one) of the grammatical object of the article. By way of example, "an element" means one element or more than one element.

The term "active ingredient" refers to glargine insulin and other insulins.

As used herein, amino acids are represented by the full name thereof, by the three letter code corresponding thereto, as indicated in the following table:

| Full Name | Three-Letter Code |
|---|---|
| Alanine | Ala |
| Arginine | Arg |
| Asparagine | Asn |
| Aspartic Acid | Asp |
| Cysteine | Cys |
| Cystine | Cys—Cys |
| Glutamic Acid | Glu |

-continued

| Full Name | Three-Letter Code |
|---|---|
| Glutamine | Gln |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

The term "lower" means the group it is describing contains from 1 to 6 carbon atoms.

The term "alkyl", by itself or as part of another substituent means, unless otherwise stated, a straight, branched or cyclic chain hydrocarbon having the number of carbon atoms designated (i.e. $C_1$-$C_6$ means one to six carbons) and includes straight, branched chain or cyclic groups. Examples include: methyl, ethyl, propyl, isopropyl, butyl, isobutyl, tert-butyl, pentyl, neopentyl, hexyl, cyclohexyl and cyclopropylmethyl. Most preferred is ($C_1$-$C_3$) alkyl, particularly ethyl, methyl and isopropyl.

The term "alkylene", by itself or as part of another substituent means, unless otherwise stated, a straight, branched or cyclic chain hydrocarbon having two substitution sites, e.g., methylene ($-CH_2-$), ethylene ($-CH_2CH_2-$), isopropylene ($-CH(CH_3)=CH_2$), etc.

The term "aryl", employed alone or in combination with other terms, means, unless otherwise stated, a cyclic carbon ring structure, with or without saturation, containing one or more rings (typically one, two or three rings) wherein such rings may be attached together in a pendant manner, such as a biphenyl, or may be fused, such as naphthalene. Examples include phenyl; anthracyl; and naphthyl. The structure can have one or more substitution sites where functional groups, such as alcohol, alkoxy, amides, amino, cyanides, halogen, and nitro, are bound.

The term "arylloweralkyl" means a functional group wherein an aryl group is attached to a lower alkylene group, e.g., $-CH_2CH_2$-phenyl.

The term "alkoxy" employed alone or in combination with other terms means, unless otherwise stated, an alkyl group or an alkyl group containing a substituent, such as a hydroxyl group, having the designated number of carbon atoms connected to the rest of the molecule via an oxygen atom, such as, for example, $-OCHOH-$, $-OCH_2OH$, methoxy ($-OCH_3$), ethoxy ($-OCH_2CH_3$), 1-propoxy ($-OCH_2CH_2CH_3$), 2-propoxy (isopropoxy), butoxy ($-OCH_2CH_2CH_2CH_3$), pentoxy ($-OCH_2CH_2CH_2CH_2CH_3$), and the higher homologs and isomers.

The term "acyl" means a functional group of the general formula $-C(=O)-R$, wherein $-R$ is hydrogen, hydrocarbyl, amino or alkoxy. Examples include acetyl ($-C(=O)CH_3$), propionyl ($-C(=O)CH_2CH_3$), benzoyl ($-C(=O)C_6H_5$), phenylacetyl ($-C(=O)CH_2C_6H_5$), carboethoxy ($-CO_2CH_2CH_3$), and dimethylcarbamoyl ($-C(=O)N(CH_3)_2$).

The terms "halo" or "halogen" by themselves or as part of another substituent mean, unless otherwise stated, a fluorine, chlorine, bromine, or iodine atom.

The term "heterocycle" or "heterocyclyl" or "heterocyclic" by itself or as part of another substituent means, unless otherwise stated, an unsubstituted or substituted, stable, mono- or multicyclic heterocyclic ring system which consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure. Examples include pyrrole, imidazole, benzimidazole, phthalein, pyridenyl, pyranyl, furanyl, thiazole, thiophene, oxazole, pyrazole, 3-pyrroline, pyrrolidene, pyrimidine, purine, quinoline, isoquinoline, carbazole, etc.

The term "chromium target molecule complex" refers to a complex comprising a plurality of chromium (Cr) atoms capable of accepting up to six ligands contributed by multivalent molecules, such as ligands from numerous molecules of N-(2,6-diisopropylphenylcarbamoylmethyl)iminodiacetic acid forming a complicated polymeric structure linked in a three-dimensional array. The complex is linked in a polymeric structure that is insoluble in water but soluble in organic solvents.

The term "supra-molecular lipid construct" refers to a lipid and/or phospholipid particle in which individual lipid molecules cooperatively interact to create a bipolar lipid membrane that encloses and isolates a portion of the medium in which the construct resides.

A "complexing agent" is a compound that forms a complex with a selected metal bridging agent, e. g. a salt of chromium, zirconium, etc., that exhibits polymeric properties. The polymeric complex is substantially insoluble in water and soluble in organic solvents.

By "substantially insoluble" is meant that a polymeric complex, such as a polymeric chromium target molecule complex or other metal targeting complexes, exhibits the property of being insoluble in water at room temperature. Such a polymeric complex, which may be crystalline, amorphous in composition, or a dissociated form thereof, when associated with a supra-molecular lipid construct forms a transport agent that carries and delivers glargine insulin to hepatocytes in the liver.

The term "associated with" means that the referenced material is incorporated into or on the surface of, or within the supra-molecular lipid construct matrix.

The terms "glargine" and "glargine insulin" both refer to a recombinant human insulin analog which differs from human insulin in that the amino acid asparagine at position A21 is replaced by glycine and two arginines are added to the C-terminus of the B-chain. Chemically, it is $21^A$-Gly-$30^B$a-L-Arg-$30^B$b-L-Arg-human insulin and has the empirical formula $C_{267}H_{404}N_{72}O_{78}S_6$ and a molecular weight of 6063. The structural formula of glargine insulin is provided in FIG. 1.

The term "non-glargine insulin" refers at all insulins, either natural or recombinant that are not glargine insulin. The term includes insulin-like moieties, including fragments of insulin molecules, that have biological activity of insulins. Examples of non-glargine insulins include, but are not limited to recombinant human regular insulin, recombinant human insulin isophane, recombinant human regular insulin, insulin aspart, insulin lispro, insulin lente, and insulin ultralente.

The term "free insulin" refers to an insulin that is not associated with a target molecule complex.

"HDV", or "Hepatocyte Delivery Vehicle", is a water insoluble target molecule complex comprising a supra-molecular lipid construct matrix containing multiple linked individual units of a structure formed by the combination of a metal bridging agent and a complexing agent. "HDV" is described in WO 99/59545, Targeted Liposomal Drug Delivery System.

"HDV-glargine" is a designation for a hepatocyte targeted composition comprising a mixture of free glargine insulin and glargine insulin associated with a water insoluble target molecule complex, wherein the complex comprises multiple linked individual units of chromium and N-(2,6-diisopropylphenylcarbamoylmethyl) iminodiacetic acid, formed by the combination of a metal bridging agent and a complexing agent, and a supra-molecular lipid construct matrix.

The term "treat" means to reduce the frequency with which symptoms of a disease, disorder, or adverse condition, and the like, are experienced by a patient.

The term "pharmaceutically acceptable carrier" means a chemical composition with which the active ingredient may be combined and which, following the combination, can be used to administer the active ingredient to a subject.

The term "physiologically acceptable" means that the ingredient is not deleterious to the subject to which the composition is to be administered.

Description of the Invention

Composition

The structure of glargine insulin is provided in FIG. 1. Glargine insulin differs from human insulin in that glargine insulin has a molecular structure that replaces asparagine with glycine at the C-terminal end of the A chain of human insulin and adds the dipeptide of arginine at the C-terminal end of the B chain of human insulin. The isoelectric point of a compound is the pH at which the overall charge of the compound is neutral. However, regions of negative and positive charges still remain within the compound. The isoelectric point of human insulin is at pH 5.3. The isoelectric point of glargine insulin is higher than human insulin because the amino acid substitutions in glargine insulin raise the isoelectric point of glargine insulin to pH 5.8-6.2. Compounds are generally less soluble in aqueous solutions at pH ranges around the isoelectric point. A compound is generally more soluble in aqueous systems where the pH of the solution is approximately 1-2 pH units higher or lower than the isoelectric point. The higher isoelectric point allows glargine insulin to remain soluble in a mildly acidic environment over a broader pH range.

LANTUS® (insulin glargine [rDNA origin] injection) is a sterile solution of glargine insulin for use as an injectable insulin for diabetic patients for subsequent management of glucose levels in vivo. Glargine insulin is a recombinant human insulin analog that is a long-acting (up to 24-hour duration of action), parenteral blood-glucose-lowering agent. LANTUS is produced by recombinant DNA technology utilizing a non-pathogenic laboratory strain of *Escherichia coli* (K12) as the production organism. LANTUS consists of glargine insulin dissolved in a clear aqueous fluid. Each milliliter of LANTUS (insulin glargine injection) contains 100 IU (3.6378 mg) glargine insulin, 30 mcg zinc, 2.7 mg m-cresol, 20 mg glycerol 85%, and water for injection. The pH of commercially available LANTUS insulin can be adjusted by addition of aqueous solutions of acids, bases or buffers that are physiologically compatible. LANTUS has a pH of approximately 4.

Figure 2:
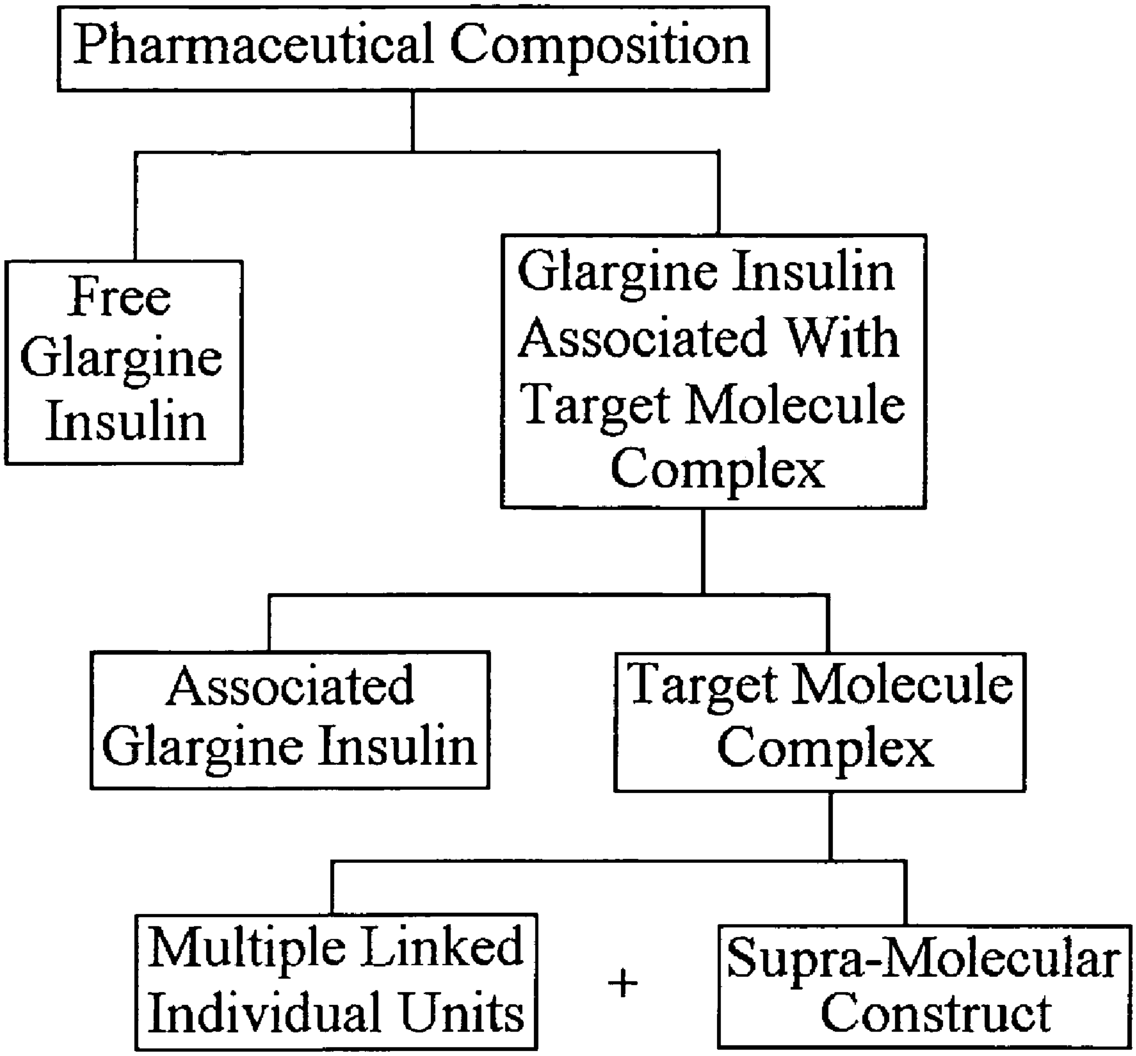
FIG. 2 is a depiction of a pharmaceutical composition that combines free glargine insulin and glargine insulin associated with a water insoluble target molecule complex.

A depiction of a pharmaceutical composition that combines free glargine insulin and glargine insulin associated with a target molecule complex is shown in FIG. 2. The target molecule complex comprises multiple linked individual units formed by complexing a bridging component with a complexing agent. The bridging component is a water soluble salt of a metal capable of forming a water-insoluble coordinated complex with a complexing agent. A suitable metal is selected from the transition and inner transition metals or neighbors of the transition metals. The transition and inner transition metals from which the metal can be selected are: Sc (scandium), Y (yttrium), La (lanthanum), Ac (actinium), the actinide series; Ti (titanium), Zr (zirconium), Hf (hafnium), V (vanadium), Nb (niobium), Ta (tantalum), Cr (chromium), Mo (molybdenum), W (tungsten), Mn (manganese), Tc (technetium), Re (rhenium), Fe (iron), Co (cobalt), Ni (nickel), Ru (ruthenium), Rh (rhodium), Pd (palladium), Os (osmium), Ir (iridium), and Pt (platinum). The neighbors of the transition metals from which the metal can be selected are: Cu (copper), Ag (silver), Au (gold), Zn (zinc), Cd (cadmium), Hg (mercury), Al (aluminum), Ga (gallium), In (indium), Tl (thallium), Ge (germanium), Sn (tin), Pb (lead), Sb (antimony) and Bi (bismuth), and Po (polonium). Examples of metal compounds useful as bridging agents include chromium chloride (III) hexahydrate; chromium (III) fluoride tetrahydrate; chromium (III) bromide hexahydrate; zirconium (IV) citrate ammonium complex; zirconium (IV) chloride; zirconium (IV) fluoride hydrate; zirconium (IV) iodide; molybdenum (III) bromide; molybdenum (III) chloride; molybdenum (IV) sulfide; iron (III) hydrate; iron (III) phosphate tetrahydrate and iron (III) sulfate pentahydrate.

The complexing agent is a compound that forms a water insoluble coordinated complex with a bridging component. There are several families of suitable complexing agents.

A complexing agent can be selected from the family of iminodiacetic acids of the formula (1) where $R_1$ is loweralkyl, aryl, arylloweralkyl, and a heterocyclic substituent.

(1)

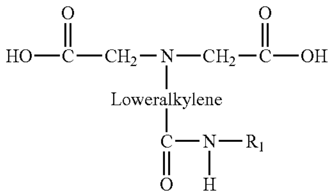

Suitable compounds of the formula (1) include:

N-(2,6-diisopropylphenylcarbamoylmethyl)iminodiacetic acid;

N-(2,6-diethylphenylcarbamoylmethyl)iminodiacetic acid;

N-(2,6-dimethylphenylcarbamoylmethyl)iminodiacetic acid;

N-(4-isopropylphenylcarbamoylmethyl)iminodiacetic acid;

N-(4-butylphenylcarbamoylmethyl)iminodiacetic acid;

N-(2,3-dimethylphenylcarbamoylmethyl)iminodiacetic acid;

N-(2,4-dimethylphenylcarbamoylmethyl)iminodiacetic acid;

N-(2,5-dimethylphenylcarbamoylmethyl)iminodiacetic acid;

N-(3,4-dimethylphenylcarbamoylmethyl)iminodiacetic acid;

N-(3,5-dimethylphenylcarbamoylmethyl)iminodiacetic acid;

N-(3-butylphenylcarbamoylmethyl)iminodiacetic acid;

N-(2-butylphenylcarbamoylmethyl)iminodiacetic acid;

N-(4-tertiary butylphenylcarbamoylmethyl)iminodiacetic acid;

N-(3-butoxyphenylcarbamoylmethyl)iminodiacetic acid;

N-(2-hexyloxyphenylcarbamoylmethyl)iminodiacetic acid;

N-(4-hexyloxyphenylcarbamoylmethyl)iminodiacetic acid;

aminopyrrol iminodiacetic acid;

N-(3-bromo-2,4,6-trimethylphenylcarbamoylmethyl)iminodiacetic acid;

benzimidazole methyl iminodiacetic acid;

N-(3-cyano-4,5-dimethyl-2-pyrrylcarbamoylmethyl)iminodiacetic acid;

N-(3-cyano-4-methyl-5-benzyl-2-pyrrylcarbamoylmethyl) iminodiacetic acid; and

N-(3-cyano-4-methyl-2-pyrrylcarbamoylmethyl)iminodiacetic acid and other derivatives of N-(3-cyano-4-methyl-2-pyrrylcarbamoylmethyl)iminodiacetic acid of formula (2), (2)

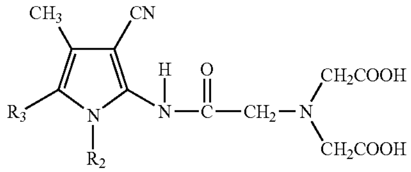

where $R_2$ and $R_3$ are the following:

| $R_2$ | $R_3$ |
|---|---|
| H | iso-$C_4H_9$ |
| H | $CH_2CH_2SCH_3$ |
| H | $CH_2C_6H_4$-p-OH |
| $CH_3$ | $CH_3$ |
| $CH_3$ | iso-$C_4H_9$ |
| $CH_3$ | $CH_2CH_2SCH_3$ |
| $CH_3$ | $C_6H_5$ |
| $CH_3$ | $CH_2C_6H_5$ |
| $CH_3$ | $CH_2C_6H_4$-p-$OCH_3$ |

A complexing agent can be selected from the family of imino diacid derivatives of the general formula (3), where $R_4$, $R_5$, and $R_6$ are independent of each other and can be hydrogen, loweralkyl, aryl, arylloweralkyl, alkoxyloweralkyl, and heterocyclic.

(3)

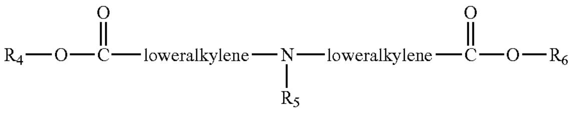

Suitable compounds of the formula (3) include: N'-(2-acetylnaphthyl) iminodiacetic acid (NAIDA); N'-(2-naphthylmethyl)iminodiacetic acid (NMIDA); iminodicarboxymethyl-2-naphthylketone phthalein complexone; 3β:7α:12α: trihydroxy-24-norchol anyl-23-iminodiacetic acid; benzimidazole methyl iminodiacetic acid; and N-(5,pregnene-3-β-ol-2-oyl carbamoylmethyl)iminodiacetic acid.

A complexing agent can be selected from the family of amino acids of formula (4), (4)

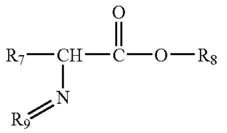

where $R_7$ is an amino acid side chain, $R_8$ is loweralkyl, aryl, arylloweralkyl, and $R_9$ is pyridoxylidene.

Some suitable amino acids of the formula (4) are aliphatic amino acids, including glycine, alanine, valine, leucine, and isoleucine; hydroxyamino acids, including serine, and threonine; dicarboxylic amino acids and their amides, including aspartic acid, asparagine, glutamic acid, and glutamine; amino acids having basic functions, including lysine, hydroxylysine, histidine, and arginine; aromatic amino acids, including phenylalanine, tyrosine, tryptophan, and thyroxine; and sulfur-containing amino acids, including cystine and methionine. Other amino acids and derivatives of biological importance include, but are not necessarily limited to (3-alanine,y-amino) butyric acid, O-diazoacetylserine (azaserine), homoserine, omithine, citrulline, and penicillamine.

Members of the pyridoxylidene class of complexing agents include, but are not limited to: pyridoxylidene glutamate; pyridoxylidene isoleucine; pyridoxylidene phenylalanine; pyridoxylidene tryptophan; pyridoxylidene-5-methyl tryptophan; pyridoxylidene-5-hydroxytryptamine; and pyridoxylidene-5-butyltryptamine.

A complexing agent can be selected from the family of diamines of the general formula (6), (6)

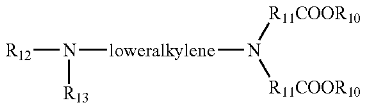

where $R_{10}$ is hydrogen, loweralkyl, or aryl; $R_{11}$ is loweralkylene or arylloweralky; $R_{12}$ and $R_{13}$ independently are hydrogen, loweralkyl, alkyl, aryl, arylloweralkyl, acylheterocyclic, toluene, sulfonyl or tosylate.

Some suitable complexing agent diamines of the formula (6) include, but are not limited to, ethylenediamine-N,N diacetic acid; ethylenediamine-N,N-bis(-2-hydroxy-5-bromophenyl) acetate; N'-acetylethylenediamine-N,N diacetic acid; N'-benzoyl ethylenediamine-N,N diacetic acid; N'-(p-toluenesulfonyl) ethylenediamine-N,N diacetic acid; N'-(p-t-butylbenzoyl) ethylenediamine-N,N diacetic acid; N'-(benzenesulfonyl) ethylenediamnine-N,N diacetic acid; N'-(p-chlorobenzenesulfonyl) ethylenediamine-N,N diacetic acid; N'-(p-ethylbenzenesulfonyl ethylenediamine-N,N diacetic acid; N'-acyl and N'-sulfonyl ethylenediamine-N,N-diacetic acid; N'-(p-n-propylbenzenesulfonyl) ethylenediamine-N,N diacetic acid; N'-(naphthalene-2-sulfonyl) ethylenediamine-N,N diacetic acid; and N'-(2,5-dimethylbenzenesulfonyl) ethylenediamine-N,N diacetic acid.

Other suitable complexing agents include: penicillamine; p-mercaptoisobutyric acid; dihydrothioctic acid; 6-mercaptopurine; kethoxal-bis(thiosemicarbazone); Hepatobiliary Amine Complexes, 1-hydrazinophthalazine (hydralazine); sulfonyl urea; Hepatobiliary Amino Acid Schiff Base Complexes; pyridoxylidene glutamate; pyridoxylidene isoleucine; pyridoxylidene phenylalanine; pyridoxylidene tryptophan; pyridoxylidene 5-methyl tryptophan; pyridoxylidene-5-hydroxytryptamine; pyridoxylidene-5-butyltryptamine; tetracycline; 7-carboxy-p-hydroxyquinoline; phenolphthalein; eosin I bluish; eosin I yellowish; verograffin; 3-hydroxyl-4-formyl-pyridene glutamic acid; and Azo substituted iminodiacetic acid.

Suitable complexing agents include: hepatobiliary dye complexes, such as rose bengal; congo red; bromosulfophthalein; bromophenol blue; toluidine blue; and indocyanine green; hepatobiliary contrast agents, such as iodipamide; and ioglycamic acid; bile salts, such as bilirubin; cholgycyliodohistamine; and thyroxine; hepatobiliary thio complexes, such as penicillamine; p-mercaptoisobutyric acid; dihydrothiocytic acid; 6-mercaptopurine; and kethoxal-bis (thiosemicarbazone); hepatobiliary amine complexes, such as 1-hydrazinophthalazine (hydralazine); and sulfonyl urea; hepatobiliary amino acid Schiff Base complexes, including pyridoxylidene-5-hydroxytryptamine; and pyridoxylidene-5-butyltryptamine; hepatobiliary protein complexes, such as protamine; ferritin; and asialo-orosomucoid; and asialo complexes, such as lactosaminated albumin; immunoglobulins, G, IgG; and hemoglobin.

The three-dimensional structure made from combining bridging agents and complexing agents is described in WO 99/59545, which is incorporated by reference. In an embodiment, the bridging agent is a metal salt, such as chromium chloride hexahydrate, that forms a coordinated complex with complexing agents, such as N-(2,6-diisopropylphenylcarbamoylmethyl)iminodiacetic acid. The bridging agent and the complexing agents are combined to form a complex comprising multiple linked units in a three-dimensional array. In a preferred embodiment, the complex comprises multiple units of chromium poly(bis)[N-(2,6-diisopropylphenylcarbamoylmethyl)iminodiacetic acid] linked together in a polymeric type structure. In an embodiment, the chromium target molecule complex substance is soluble in a mixture of lipids containing 1,2-distearoyl-sn-glycero-3-phosphocholine, dicetyl phosphate and cholesterol.

The complex is incorporated within a supra-molecular lipid construct, comprised of lipids or groups of lipids, to form a water insoluble target molecule complex, as described in WO 99/59545. A suitable lipid, or a mixture of lipids where lipid molecules function individually or in combination thereof, will dissolve the metal complex and form a supra-molecular lipid construct that incorporates the metal complex therein. A suitable lipid is selected from a group of lipids commonly employed to form supra-molecular lipid constructs. Suitable lipids include 1,2-distearoyl-sn-glycero-3-phosphocholine, 1,2-dipalmitoyl-sn-glycero-3-phosphocholine, 1,2-dimyristoyl-sn-glycero-3-phosphocholine, cholesterol, cholesterol oleate, dicetylphosphate, 1,2-distearoyl-sn-glycero-3-phosphate, 1,2-dipalmitoyl-sn-glycero-3-phosphate, 1,2-dimyristoyl-sn-glycero-3-phosphate, and a mixture of any of the foregoing lipids or appropriate derivative of these lipids. In a preferred embodiment the lipids are a mixture of 1,2-distearoyl-sn-glycero-3-phosphocholine, cholesterol, and dicetyl phosphate. The selected lipid, or mixture of lipids, is maintained in suspension in aqueous media to form a structure able to incorporate glargine insulin into the structure. In an embodiment, a mixture of the target molecule complex and the supra-molecular lipid construct is also provided with a masking agent in intimate association therewith to protect it from immunoreactive attack, such as by macrophages.

Adjustment of the pH of an aqueous solution surrounding the supra-molecular lipid construct containing the target molecule complex, by the addition of acids, bases or buffers, results in a negative charge in the supra-molecular lipid construct structure. The pH range at which this occurs depends upon the composition of the lipids. A preferred lipid system is a mixture of 1,2-distearoyl-sn-glycero-3-phosphocholine, cholesterol and dicetylphosphate. This mixture forms a negatively charged supra-molecular lipid construct structure under physiological conditions. The supra-molecular lipid construct exhibits hepatocyte targeting specificity, i.e. is specific for cellular hepatocytes, thereby allowing the construct to be targeted to the liver.

A pharmaceutical composition comprises a mixture of free glargine insulin and glargine insulin associated with a water insoluble target molecule complex. Free glargine insulin is the material depicted in FIG. 1. Free glargine insulin is not associated with the target molecule complex and is soluble in water. The other form of glargine insulin in the composition is associated with a water insoluble target molecule complex.

It has been discovered in the present invention that when the appropriate lipid components are formulated into a water insoluble target molecule complex using Sterile Water for Injection, USP (SWI) that has been terminally pH adjusted to pH 3.95±0.2, the overall electronic charge on the target molecule complex is predominately negative. Glargine insulin has a net positive charge at pH 5.2±0.5, which is below the isoelectric point of the protein. The positive charge on glargine insulin at pH 5.2±0.5 allows for interaction of the positively charged portion of glargine insulin with the negatively charge portion of the target molecule complex. This results in positively charged glargine insulin being attracted to the negatively charged target molecule complex. Portions of the charged glargine insulin become associated with charges on the lipids and the charged glargine insulin moves within the lipids, while other charged glargine insulin molecules are sequestered within the core volume of the supra-molecular lipid construct after partitioning through the various lipid moieties of the supra-molecular construct.

There is an equilibrium between free glargine insulin in solution and glargine insulin associated with the water insoluble target molecule complex. Because the interactions between glargine insulin and the target molecule complex involve equilibria, over time free glargine insulin is able to further bind and partition into the lipid domains and/or the central core volume of the water insoluble target molecule complex. In an embodiment, free glargine insulin can be transformed into transitory lipid derivatives by adsorbing onto, or reacting with, individual molecules of lipid that are in equilibrium with the water insoluble target molecule complex. These derivatives associate with the lipids of the water insoluble target molecule complex and enter the core-volume of the complex, thus affecting the pharmacological activity of the product.

When a composition of the present invention is administered by injection, the pharmacological activity of the composition in terms of bioavailability will be realized when the supra-molecular lipid construct is located in the subcutaneous depot in vivo at pH 5.8-pH 6.2, where free glargine insulin is precipitated in an insoluble form. The release of free insulin from the supra-molecular lipid construct is controlled by a biokinetic release mechanism. The targeted supra-molecular lipid construct with the remaining insulin is also controlled by a biokinetic release mechanism regulated by an equilibrium between the insoluble to soluble forms of glargine insulin in the subcutaneous depot as insoluble insulin solubilizes in response to physiological conditions.

Description of the Invention

Method of Manufacture

FIG. 3 demonstrates an outline for a process for manufacturing a mixture of free glargine insulin and glargine insulin associated with a water insoluble target molecule complex.

In an embodiment, the manufacture of the composition involves three overall steps: preparing a target molecule complex, incorporating the target molecule complex into a supra-molecular lipid construct, and combining the target molecule complex with glargine insulin to form a pharmaceutical composition.

The target molecule complex comprises multiple individual units linked together in a polymeric array. Each unit comprises a bridging component and a complexing agent. In an embodiment, the target molecule complex is formed by combining the selected metal compound, e. g. chromium chloride (III) hexahydrate, with an aqueous buffered solution of the complexing agent. In an embodiment, an aqueous buffered solution of the complexing agent is prepared by dissolving a complexing agent, e.g., N-(2,6-diisopropylphenylcarbamoylmethyl)iminodiacetic acid, in an aqueous buffered solution, e.g., 10 mM sodium acetate buffer at a final pH of 3.2-3.3. A metal compound is added in excess in an amount sufficient to complex with an isolatable portion of the complexing agent, and the reaction is conducted at a temperature of approximately 20° C. to 33° C. for approximately 24 to 96 hours, or until the resultant complex precipitates out of the aqueous buffered solution. The precipitated complex is then isolated for future use.

The precipitated complex is then mixed with the selected lipids or the lipids of the supra-molecular lipid construct and dissolved in an organic solvent. In an embodiment, the organic solvent is chloroform:methanol (2:1 v/v). The lipids are in a concentration sufficient to dissolve and incorporate either all or a portion of the metal complex therein. The mixture of the complex and the selected lipids that form the supra-molecular lipid construct are maintained at a temperature of approximately 60° C. when a high transition temperature lipid, such as 1,2-distearoyl-sn-glycero-3-phosphocholine, is employed. Lower temperatures may be used depending upon the transition temperature of the lipids selected for incorporation into the supra-molecular lipid construct. A time period from 30 minutes to 2 hours under vacuum is generally required to dry the lipids and remove any residual organic solvent from the lipid matrix in order to form the target molecule complex intermediate.

Lipids can be produced and loaded by the methods disclosed herein, and those methods described in U.S. Pat. Nos. 4,946,787; 4,603,044; and 5,104,661, and the references cited therein. Typically, the aqueous supra-molecular lipid construct formulations of this invention will comprise 0.1% to 10% active agent by weight (i.e. 1-100 mg drug per ml), and 0.1% to 4% lipid by weight in an aqueous solution, optionally containing salts and buffers, in a quantity to make 100% by volume. Preferred are formulations which comprise 0.01% to 5% active agent. Most preferred is a formulation comprising 0.01% to 5% active agent by weight and up to 2% by weight of a lipid component in an amount of aqueous solution sufficient (q. s.) to make 100% by volume.

In an embodiment, glargine insulin was loaded into the target molecule complex after the pH of a suspension of the target molecule complex and Water for Injection, USP was adjusted from approximately pH 4.89±0.2 to 5.27±0.5. The pH of a solution of glargine insulin was adjusted from pH 3.88±0.2 to approximately pH 4.78±0.5, then the water insoluble target molecular complex was added. The resulting composition was a mixture of free glargine insulin and glargine insulin associated with a water insoluble target molecule complex. A portion of glargine insulin became associated with the supra-molecular lipid construct matrix or entrapped in the core volume of the supra-molecular lipid construct. This pharmaceutical composition is also referred to as HDV-glargine. In an embodiment, an aliquot of the target molecule complex is introduced into a vial of Glargine Insulin containing 100 International units of insulin/ml to provide a hepatocyte specific delivery system containing both free glargine insulin and glargine insulin associated with the target molecule complex.

A pharmaceutical composition that combines free glargine insulin and glargine insulin associated with a water insoluble target molecule complex was prepared by the following procedure. The pH of a sample of Sterile Water for Injection, USP, was adjusted to pH 3.95±0.2. An aliquot of HDV suspension was taken and its pH was adjusted in a series of steps until the final pH was 5.2±0.5. An aliquot of the Sterile Water for Injection, USP, at pH 3.95±0.2 was mixed with the suspension of the target molecule complex. The pH of the resulting suspension was 4.89±0.2. The pH of this suspension was then adjusted to pH 5.27±0.5. The pH of an aliquot of glargine insulin was adjusted from pH 3.88±0.2 to pH 4.78±0.5. This solution was then added to the suspension of the target molecule complex at pH 5.20±0.5. The resulting pharmaceutical composition is a mixture of free glargine insulin and glargine insulin associated with a water insoluble target molecule complex. This pharmaceutical composition is also referred to as HDV-glargine.

Description of the Invention

Method of Use

Patients with Type I or Type II diabetes are administered an effective amount of a hepatocyte targeted composition comprising a mixture of free glargine insulin and glargine insulin associated with a water insoluble target molecule complex. In an embodiment, glargine insulin can be combined with other forms of insulin, such as the rapid acting lispro insulin and insulin aspart, short acting Regular insulin, intermediate acting lente insulin or recombinant human insulin isophane, and long acting ultralente insulin, or premixed combinations of insulins. In an embodiment, the composition can be administered by a subcutaneous or oral route.

After a composition is administered to a patient by subcutaneous injection, the in situ physiological environment in the injection area, the morphology and chemical structures of free glargine insulin and the glargine insulin associated with the water insoluble target molecule complex begin to change. As the pH of the environment around the free glargine insulin and the glargine insulin associated with the water insoluble target molecule complex increases after being diluted with physiological media, the pH reaches the isoelectric point of glargine insulin, where flocculation, aggregation and precipitation reactions occur for both free glargine insulin and glargine insulin associated with the target molecule complex. The rates at which these processes occur differ between free glargine insulin and glargine insulin associated with the target molecule complex. The free glargine insulin is directly exposed to changes in pH and dilution. Exposure of glargine insulin associated with the target molecule complex to small changes in pH and dilution at physiological pH is delayed due to the time required for diffusion of physiological fluids or media through the lipid bilayer in the water insoluble target molecule complex. The delay in the release of insulin from the supra-molecular lipid construct as well as the delay of the release of supra-molecular lipid construct with associated insulin within the precipitated free glargine matrix is an essential feature of this invention since it affects and augments the biological and pharmacological response in vivo.

Oral administration of a pharmaceutical composition that combines free glargine insulin and glargine insulin associated with a target molecule complex is followed by intestinal absorption of glargine insulin associated with the target molecule complex into the circulatory system of the body where it is also exposed to the physiological pH of the blood. All or a portion of the supra-molecular lipid construct is delivered to the liver.

As the physiological dilution is increased in situ in the subcutaneous space or upon entering into the circulatory system, the free glargine insulin and glargine insulin associated with the target molecule complex encounter a normal physiological pH environment of pH 7.4. As a result, free glargine insulin changes from a soluble form at injection, to a insoluble form at a pH near its isoelectric point of pH 5.8-6.2, and then to a soluble form at physiological pH. In the soluble form, glargine insulin migrates through the body to sites where it is capable of eliciting a pharmacological response. Glargine insulin associated with the water insoluble target molecule complex becomes solubilized and released from the complex at a different rate that is slower than that of free glargine insulin. This is because glargine insulin associated with the water insoluble target molecule complex has to traverse the core volume and lipid domains of the water insoluble target molecule complex before it contacts the bulk phase media.

The supra-molecular lipid construct structure of this invention provides a useful agent for pharmaceutical application for administering glargine insulin to a host. Accordingly, the structures of this invention are useful as pharmaceutical compositions in combination with pharmaceutically acceptable carriers. Administration of the structures described herein can be via any of the accepted modes of administration for glargine insulin that are desired to be administered. These methods include oral, parenteral, nasal and other systemic or aerosol forms.

The amount of glargine insulin administered will be dependent on the subject being treated, the type and severity of the affliction, the manner of administration and the judgment of the prescribing physician. Although effective dosage ranges for specific biologically active substances of interest are dependent upon a variety of factors, and are generally known to one of ordinary skill in the art, some dosage guidelines can be generally defined. For most forms of administration, the lipid component will be suspended in an aqueous solution and generally not exceed 4.0% (w/v) of the total formulation. The drug component of the formulation will most likely be less than 20% (w/v) of the formulation and generally greater than 0.01% (w/v).

Dosage forms or compositions containing active ingredient in the range of 0.005% to 5% with the balance made up from non-toxic carriers may be prepared.

The exact composition of these formulations may vary widely depending on the particular properties of the drug in question. However, they will generally comprise from 0.01% to 5%, and preferably from 0.05% to 1% active ingredient for highly potent drugs, and from 2%-4% for moderately active drugs.

The percentage of active compound contained in such parenteral compositions is highly dependent on the specific nature thereof, as well as the activity of the compound and the needs of the subject. However, percentages of active ingredient of 0.01% to 5% in solution are employable, and will be higher if the composition is a solid which will be subsequently diluted to the above percentages. Preferably the composition will comprise 0.2%-2.0% of the active agent in solution.

The formulations of pharmaceutical compositions described herein may be prepared by any method known or hereafter developed in the art of pharmacology. In general, such preparatory methods include the step of bringing the hepatocyte targeted composition into association with a carrier or one or more other ingredients, and then, if necessary or desirable, shaping or packaging the product into a desired single- or multi-dose unit.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of pharmaceutical compositions of the invention is contemplated include, but are not limited to, humans and other primates, mammals including commercially relevant mammals such as cattle, pigs, horses, sheep, cats, and dogs.

Pharmaceutical compositions that are useful in the methods of the invention may be prepared, packaged, or sold in formulations suitable for oral, parenteral, pulmonary, buccal, or another route of administration.

A pharmaceutical composition of the invention may be prepared, packaged, or sold in bulk, as a single unit dose, or as a plurality of single unit doses. As used herein, a "unit dose" is a discrete amount of a pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. However, delivery of the active agent as set forth in this invention may be as low as 1/10, 1/100 or 1/1,000 or smaller than the dose normally administered because of the targeted nature of the insulin therapeutic agent.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one that comprises a carbon-containing liquid molecule and exhibits a less polar character than water.

A tablet comprising the pharmaceutical composition may, for example, be made by compressing or molding a pharmaceutical composition of the invention, optionally with one or more additional ingredients. Compressed tablets may be prepared by compressing, in a suitable device, the pharmaceutical composition in a free-flowing form such as a powder or granular preparation, optionally mixed with one or more of a binder, a lubricant, an excipient, a surface active agent, and a dispersing agent. Molded tablets may be made by molding, in a suitable device, a mixture of the pharmaceutical composition, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the pharmaceutical composition. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising a pharmaceutical composition of the current invention may be made using a physiologically degradable composition, such as gelatin. Such hard capsules may further comprise additional ingredients including, for example, an inert solid diluent such as calcium carbonate, calcium phosphate, or kaolin.

Soft gelatin capsules comprising a pharmaceutical composition of the invention may further comprise a physiologically degradable composition, such as gelatin. Such soft capsules may further comprise a pharmaceutical composition of the invention mixed with water or an oil medium such as peanut oil, liquid paraffin, or olive oil.

Liquid formulations of a pharmaceutical composition of the invention that are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the pharmaceutical composition in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of a pharmaceutical composition of the invention in aqueous or oily solvents may be prepared in substantially the same manner as liquid suspensions, the primary difference being that the pharmaceutical composition is dissolved, rather than suspended in the solvent. Liquid solutions of a pharmaceutical composition of the invention may comprise each of the components described with regard to liquid suspensions, it being understood that suspending agents will not necessarily aid dissolution of the pharmaceutical composition in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical composition of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

As used herein, "parenteral administration" of a pharmaceutical composition includes any route of administration characterized by physical breaching of a tissue of a subject and administration of a pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the composition combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the pharmaceutical composition is provided in dry (i.e. powder or granular) form for reconstitution with a suitable vehicle (e.g. sterile pyrogen-free water) prior to parenteral administration of the reconstituted composition.

Pharmaceutical compositions may be prepared, packaged, or sold in the form of a sterile injectable aqueous or oily suspension or solution. This suspension or solution may be formulated according to the known art, and may comprise, in addition to the pharmaceutical composition, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally administrable formulations include those that comprise the pharmaceutical composition in microcrystalline form or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the pharmaceutical composition and which have a diameter in the range from about 0.5 to about 7 microns, and preferably from about 1 to about 6 microns. Such compositions are conveniently in the form of dry powders for administration using a device comprising a dry powder reservoir to which a stream of propellant may be directed to disperse the powder or using a self-propelling solvent/powder-dispensing container such as a device comprising the pharmaceutical composition dissolved or suspended in a low-boiling propellant in a sealed container. Preferably, such powders comprise particles wherein at least 98% of the particles by weight have a diameter greater than 0.5 microns and at least 95% of the particles by number have a diameter less than 7 microns. More preferably, at least 95% of the particles by weight have a diameter greater than 1 nanometer and at least 90% of the particles by number have a diameter less than 6 microns. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the pharmaceutical composition).

Pharmaceutical compositions of the invention formulated for pulmonary delivery may also provide the composition in the form of droplets of a solution or suspension. Such formulations may be prepared, packaged, or sold as aqueous or dilute alcoholic solutions or suspensions, optionally sterile, comprising the pharmaceutical composition, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 microns.

The formulations described herein as being useful for pulmonary delivery are also useful for intranasal delivery of a pharmaceutical composition of the invention.

Another formulation suitable for intranasal administration is a coarse powder comprising the pharmaceutical composition of the invention having an average particle from about 0.2 to 500 microns. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 75% (w/w) of the pharmaceutical composition, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) pharmaceutical composition, the balance comprising an orally dissolvable or degradable composition and, optionally, one or more of the additional ingredients described herein. Alternately, formulations suitable for buccal administration may comprise a powder or an aerosolized or atomized solution or suspension comprising a pharmaceutical composition of the invention. Such powdered, aerosolized, or aerosolized formulations, when dispersed, preferably have an average particle or droplet size in the range from about 0.1 to about 200 microns, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1%-1.0% (w/w) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a supra-molecular lipid construct preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in pharmaceutical compositions of the invention are known in the art and described, for example in Genaro, ed., 1985, *Remington's Pharmaceutical Sciences*, Mack Publishing Co., Easton, Pa., which is incorporated herein by reference.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, companion animals and other mammals.

Typically dosages of the pharmaceutical composition of the invention which may be administered to an animal, preferably a human, range in amount from 1 microgram to about 1 mg per kilogram of body weight of the animal. The precise dosage administered will vary depending upon any number of factors, including but not limited to, the type of animal and type of disease state being treated, the age of the animal and the route of administration. Preferably, the dosage of the active ingredients in the composition will vary from about 1 mg to about 10 mg per kilogram of body weight of the animal. More preferably, the dosage will vary from about 10 mg to about 1 g per kilogram of body weight of the animal.

The composition of the invention may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled physician and will depend upon any number of factors, such as, but not limited to, the type and severity of the disease being treated, the type and age of the animal, etc.

The invention also includes a kit comprising the composition of the invention and an instructional material which describes administering the composition to a tissue of a mammal. In another embodiment, this kit comprises a (preferably sterile) solvent suitable for dissolving or suspending the composition of the invention prior to administering the compound to the mammal.

As used herein, an "instructional material" includes a publication, a recording, a diagram, or any other medium of expression which can be used to communicate the usefulness of the protein of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the components of the invention or be shipped together with a container which contains the components of the invention. Alternatively, the instructional material may be shipped separately from the container with the intention that the instructional material and the compound be used cooperatively by the recipient.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Experimental Example 1

Pharmaceutical Composition

The materials and methods used in the experiments presented in this Experimental Example are now described.

A hepatocyte targeted composition comprises a mixture of free glargine insulin and glargine insulin associated with a water insoluble target molecule complex. The complex comprises multiple linked individual units and a supra-molecular lipid construct matrix, comprising a mixture of 1,2-distearoyl-sn-glycero-3-phosphocholine, cholesterol, dicetyl phosphate. The bridging agent polychromium poly(bis)[N-(2,6-diisopropylphenylcarbamoylmethyl) iminodiacetic acid] is present within the complex.

Experimental Example 2

Preparation of HDV-Glargine Insulin

An intermediate mixture of the components of a target molecule complex was produced by the following procedure. A mixture of the components [total mass of 2.830 g] of a target molecule complex was prepared by adding aliquots of the lipids 1,2-distearoyl-sn-glycero-3-phosphocholine (2.015 g), crystalline cholesterol (0.266 g), and dicetyl phosphate (0.515 g) to the bridging agent, polychromium poly (bis)[N-(2,6-diisopropylphenylcarbamoylmethyl) iminodiacetic acid] (0.034 g). A solution of chloroform (50 ml) and methanol (25 ml) had been dehydrated over molecular sieves. The mixture of the components of the target molecule complex was added to the chloroform/methanol solution, which was then placed in a water bath at 60° C.±2° C. to form a solution. The chloroform/methanol solution was removed under vacuum on a rotary evaporator using an aspirator, followed by a vacuum pump, and the solid intermediate mixture formed.

A target molecule complex was produced by the following process. The pH of 530 ml of Sterile Water for Injection, USP (SWI) was adjusted to between pH 6.5-7.5 by the addition of a 105 μl of 0.1 N NaOH solution. Sufficient water was added to make 200 g of product. The pH adjusted SWI was added to the intermediate mixture (2.830 g) and the intermediate mixture was hydrated by placing the mixture in a water bath at 80° C.±2° C. while rotating the mixture for approximately 30 minutes±15 minutes, or until the mixture was a uniform appearing suspension. During the previous process, the pH of the suspension decreased. The pH of the suspension was then adjusted to pH 5.44±0.5 pH units by the addition of approximately 1.0 ml 0.1 N NaOH.

The suspension of the hydrated target complex was transferred to a model M-110 EHI microfluidizer that was preheated to 70° C.±10° C. with 28 mM sodium phosphate buffer at pH 7.0. The suspension was microfluidized at 9,000 psig using one pass of the suspension of the hydrated target molecule complex through the fluidizer. After passing through the microfluidizer, an unfiltered sample (2.0-5.0 ml) of the fluidized suspension was collected for particle size analysis using unimodal distribution data from a Coulter N-4 plus particle size analyzer. Prior to all particle size determinations, the sample was diluted with 0.2 micron filtered SWI that has been pH adjusted to between 6.5-7.5. The particle size was required to range from 0.020-0.40 microns. If the particle size was not within this range, the suspension was passed through the microfluidizer again, and the particle size was analyzed again until the particle size requirements was reached. The microfluidized target molecule complex was collected in a sterile container.

The suspension of the microfluidized target molecule complex was maintained at 60° C.±2° C. while filtered twice through a sterile 0.8 micron+0.2 micron gang filter attached to a 5.0 ml syringe. An aliquot of the filtered suspension was analyzed to determine the particle size range of particles in the suspension. The particle size of the final 0.2 micron filtered sample was in the range from 0.0200-0.2000 microns, as determined from the unimodal distribution printout from the particle size analyzer. The pH of the filtered suspension of the target molecule complex was 3.74±0.2 pH units before pH adjustment. Samples were stored in a refrigerator between 2°-8° C. until further use.

The pharmaceutical composition comprising a mixture of free glargine insulin and glargine insulin associated with a water insoluble target molecule complex, also referred to as HDV-glargine insulin, was produced was produced by the following process. The pH of a 5.0 ml aliquot of the twice filtered suspension of the target molecule complex was adjusted from an initial pH of pH 3.74±0.2 to pH 5.2±pH 0.5 by the sequential addition of sterile 0.1 NaOH according to the following procedure:

pH 3.74+10 μl 0.1 N NaOH→pH 3.96
pH 3.96+20 μl 0.1 N NaOH→pH 4.52
pH 4.52+10 μl 0.1 N NaOH→pH 4.69
pH 4.69+10 μl 0.1 N NaOH→pH 5.01
pH 5.01+10 μl 0.1 N NaOH→pH 5.20

A 1.6 ml aliquot of the target molecule complex suspension at pH 5.20±0.5 was combined with 18.4 ml of SWI, which had been adjusted to pH 3.95±0.2. The pH of the resulting suspension was adjusted from pH 4.89 to pH 5.27±0.5 by the addition of 10 μl±1.0 μl of 0.1 N NaOH.

The pH of 5.0 ml aliquot of Lantus® Glargine—U-100 Insulin was increased from pH 3.88±0.2 to pH 4.78±0.5 by the addition of 60 μl±2 μl of sterile 0.1 N NaOH with mixing. A 2.5 ml±0.1 ml aliquot of the target molecule complex suspension at pH 5.27±0.5 was added to 5.0 ml±0.1 ml of the solution of Glargine insulin at pH 4.78±0.5 to produce the pharmaceutical composition containing a mixture of free glargine insulin and glargine insulin associated with the water insoluble target molecule complex. The product contained 66.1 IU of glargine insulin/ml suspension. In an embodiment, the mixture of free glargine insulin and glargine insulin associated with the complex can be produced in a vial of glargine insulin in situ in order to manufacture individual dosage forms.

Example 3

Method of Use of HDV-Glargine Insulin for the Control of Blood Glucose in Type I Diabetes Mellitus Patients HDV-glargine insulin was administered to patients to determine the ability of HDV-glargine insulin to control post prandial blood glucose levels. Seven Type I diabetes mellitus patients were selected. The patients were carefully screened and selected according to criteria listed in the study protocol. The patients were treated with basal glargine insulin and a short-acting insulin at meal times prior to entering the HDV-glargine insulin treatment period. Patients were monitored (via diary cards and site contact) for four days prior to administering HDV-glargine insulin to assure that they were in acceptable control of their blood glucose levels. Morning fasting glucose levels were established to be in the range of 100-150 mg/dl.

During the study, the dose of HDV-glargine insulin for each patient was 1.2× their usual daily dose of basal glargine insulin to compensate for the amount of short-acting insulin that they would not receive on the test days. Blood samples were taken according to a set schedule over 13 hours. HDV was added to glargine insulin using the method previously described to produce a suspension with a final concentration of 66.1 IU glargine/ml and 0.37 mg HDV/ml. The patients were injected with HDV-glargine insulin one hour prior to the morning breakfast. At each of the three daily meals, breakfast, lunch and dinner, a 60 gram carbohydrate meal was prescribed by a dietitian.

Figure 4:
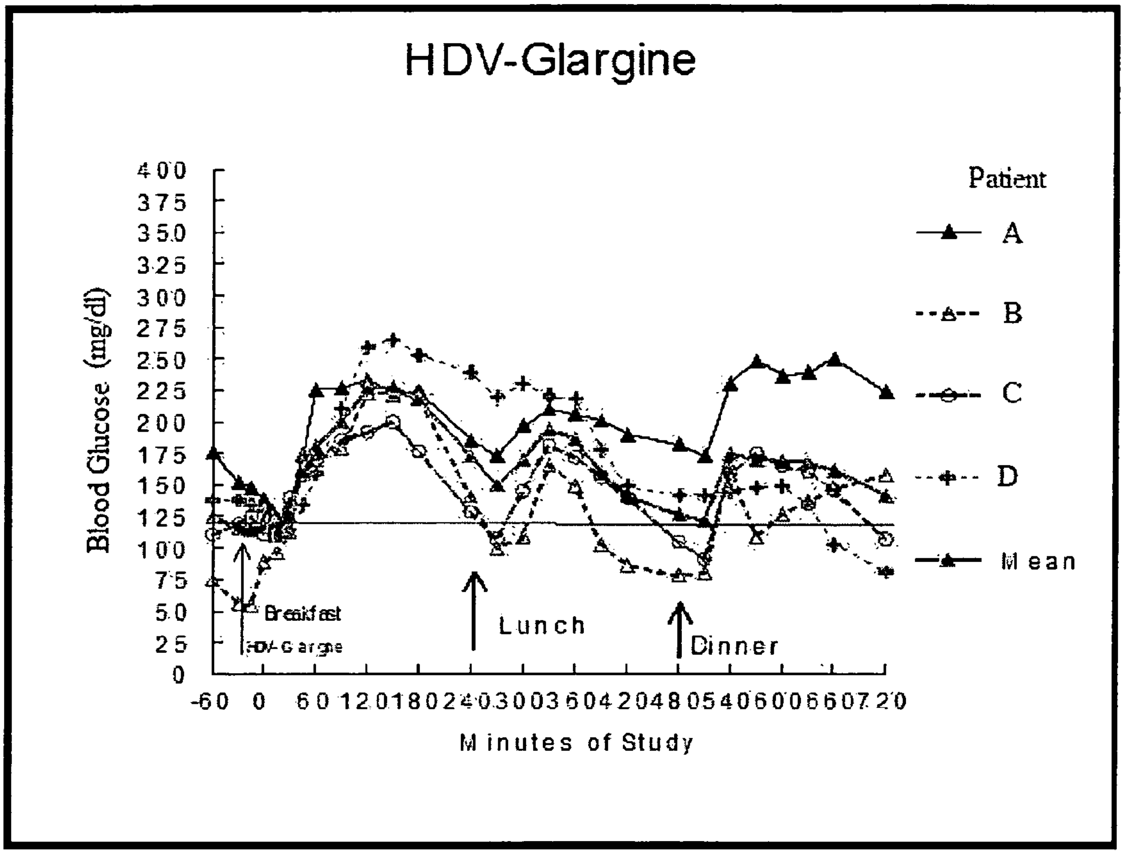
FIG. 4 is a graph of the concentrations of glucose in blood of individual patients treated once before breakfast with HDV-glargine insulin.
Figure 5:
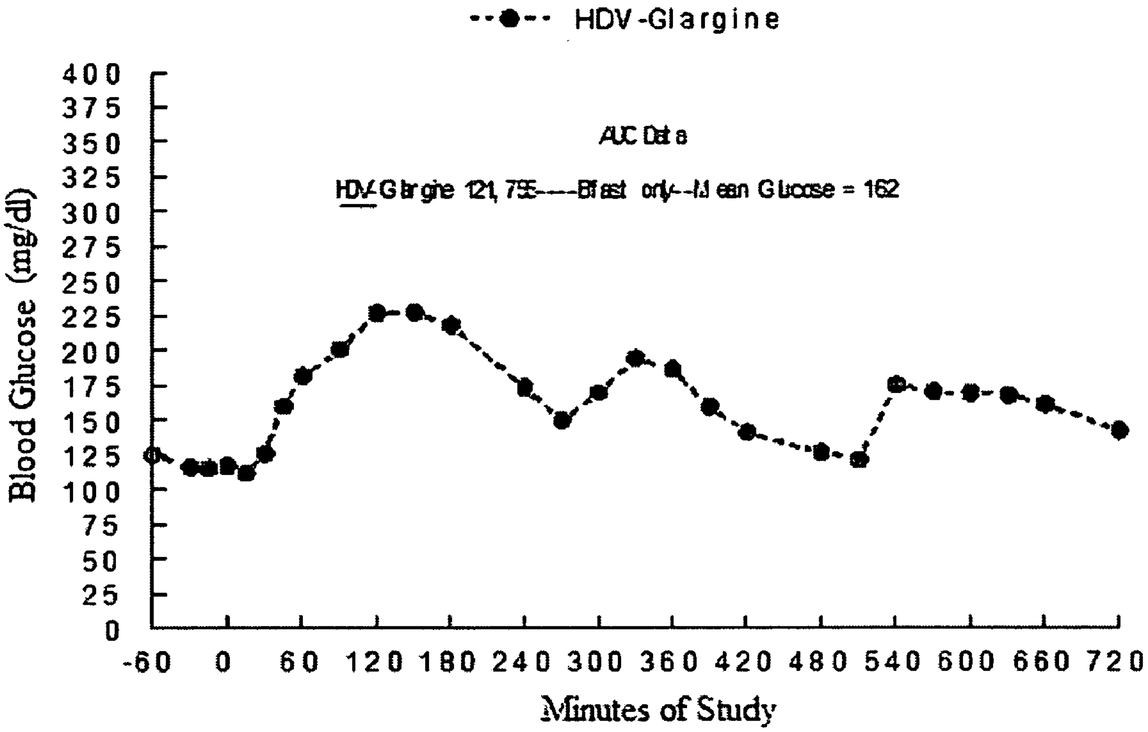
FIG. 5 is a graph of the effect of a single dose of HDV-glargine insulin on average blood glucose concentrations in patients consuming three meals during the day.
Figure 6:
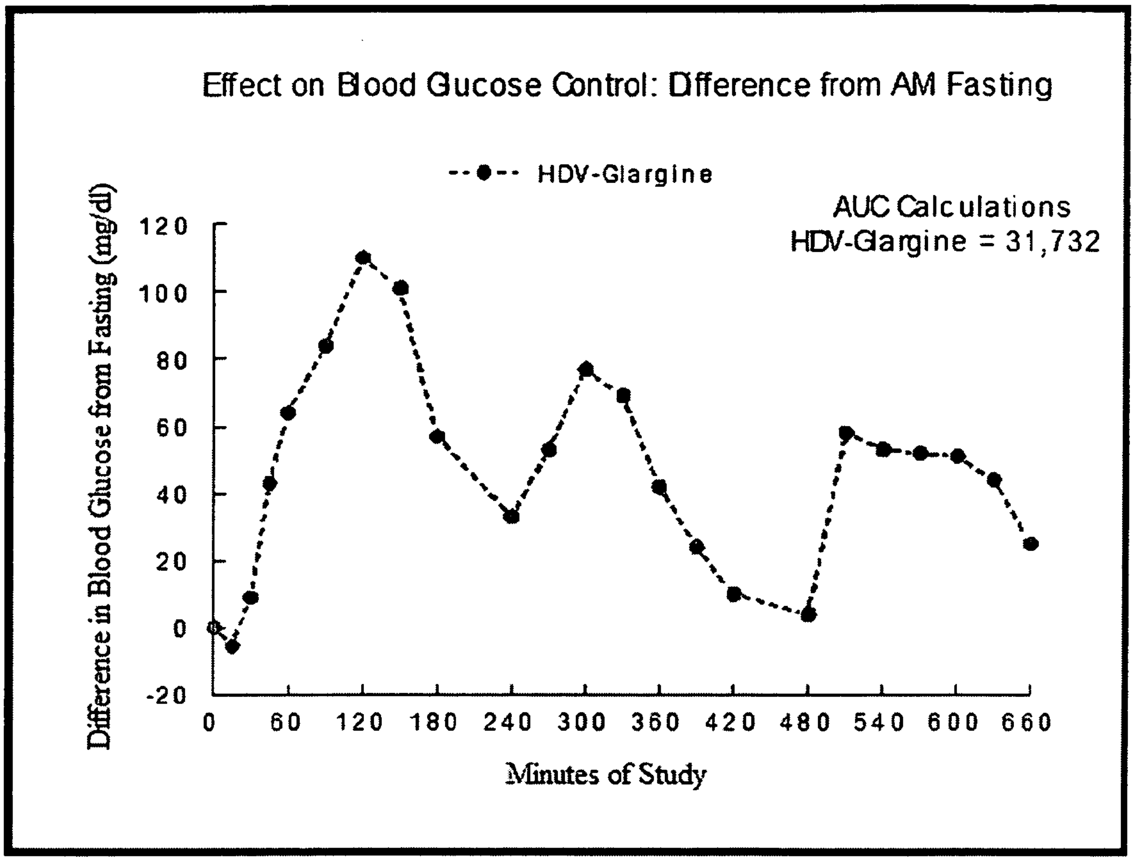
FIG. 6 is a graph of the effect of HDV-glargine insulin on blood glucose concentrations over time relative to blood glucose concentrations during fasting.

The results of the experiments presented in this Experimental Example are now described. HDV-glargine insulin was well tolerated by the patients and no adverse reactions were observed at the injection sites. Hypoglycemic reactions were not observed in patients receiving this treatment. The blood glucose values of patients treated with HDV-glargine insulin are graphically presented in FIG. 4. FIG. 4 shows that blood glucose concentrations increased, as anticipated, following meals and glucose concentrations decreased over time until the next meal was eaten. This pattern was observed for all four patients. FIG. 5 shows the effect of a single dose of HDV-glargine insulin on average blood glucose concentrations in patients consuming three meals during the day. As with the individual patients, blood glucose concentrations increased following meals and glucose concentrations decreased over time until the next meal was eaten. Average blood glucose concentrations were above the baseline value at all time points. The curve suggests that the efficacy of HDV-glargine insulin improved throughout the day because there was less variation between the high and low concentrations after the lunch and dinner meals than the breakfast meal. The effect of HDV-glargine insulin on blood glucose concentrations over time relative to blood glucose concentrations during fasting are shown in FIG. 6. Blood glucose concentrations increased following meals then decreased over time towards the glucose concentration during fasting until the next meal was eaten. Blood glucose concentrations were above fasting concentrations throughout the study. Treatment of patients with HDV-glargine insulin resulted in some degree of post-prandial blood glucose level control, indicating that HDV was able to carry sufficient quantities of glargine-insulin to the liver at mealtimes to provide this control. Blood glucose levels were typical of Type I patients that usually receive basal insulin therapy plus short-acting insulins at meal times.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A hepatocyte-targeting composition comprising:

free glargine insulin; and glargine insulin associated with a water-insoluble target molecule complex;

wherein said target molecule complex is comprised of a combination of a supra-molecular lipid construct matrix comprising at least one lipid component, and multiple linked individual units, each of said individual units comprising at least one bridging component selected from the group consisting of a transition element, an inner transition element, and a neighbor element of said transition element; and a complexing component;

wherein said complexing component comprises at least one member selected from the group consisting of:

N-(2,6-diisopropylphenylcarbamoylmethyl)iminodiacetic acid;

N-(2,6-diethylphenylcarbamoylmethyl)iminodiacetic acid;

N-(2,6-dimethylphenylcarbamoylmethyl)iminodiacetic acid;

N-(4-isopropylphenylcarbamoylmethyl)iminodiacetic acid;

N-(4-butylphenylcarbamoylmethyl)iminodiacetic acid;

N-(2,3-dimethylphenylcarbamoylmethyl)iminodiacetic acid;

N-(2,4-dimethylphenylcarbamoylmethyl)iminodiacetic acid;

N-(2,5-dimethylphenylcarbamoylmethyl)iminodiacetic acid;

N-(3,4-dimethylphenylcarbamoylmethyl)iminodiacetic acid;

N-(3,5-dimethylphenylcarbamoylmethyl)iminodiacetic acid;

N-(3-butylphenylcarbamoylmethyl)iminodiacetic acid;

N-(2-butylphenylcarbamoylmethyl)iminodiacetic acid;

N-(4-tertiary butylphenylcarbamoylmethyl)iminodiacetic acid;

N-(3-butoxyphenylcarbamoylmethyl)iminodiacetic acid;

N-(2-hexyloxyphenylcarbamoylmethyl)iminodiacetic acid;

N-(4-hexyloxyphenylcarbamoylmethyl)iminodiacetic acid;

aminopyrrol iminodiacetic acid;

N-(3-bromo-2,4,6-trimethylphenylcarbamoylmethyl)iminodiacetic acid;

benzimidazole methyl iminodiacetic acid;

N-(3-cyano-4,5-dimethyl-2-pyrrylcarbamoylmethyl)iminodiacetic acid;

N-(3-cyano-4-methyl-5-benzyl-2-pyrrylcarbamoylmethyl)iminodiacetic acid;

and N-(3-cyano-4-methyl-2-pyrrylcarbamoylmethyl)iminodiacetic acid;

provided that when said transition element is chromium, a chromium target molecule complex is created;

wherein said target molecule complex further comprises a negative charge.

2. The hepatocyte-targeting composition of claim 1, further comprising at least one free non-glargine insulin and at least one non-glargine insulin associated with a water-insoluble target molecule complex.

3. The hepatocyte-targeting composition of claim 2, wherein said non-glargine insulin is selected from the group consisting of lispro insulin, aspart insulin, regular insulin, lente insulin, ultralente insulin, recombinant human regular insulin, recombinant human insulin isophane or premixed combinations of any of the aforementioned insulins, and a combination of two or more of the aforementioned insulins.

4. A method of treating a patient for Type I or Type II diabetes comprising administering to the patient an effective amount of a hepatocyte targeted composition of claim 2, wherein said non-glargine insulin is selected from the group consisting of lispro insulin, aspart insulin, regular insulin, lente insulin, ultralente insulin, recombinant human regular insulin, recombinant human insulin isophane or premixed combinations of any of the aforementioned insulins, and a combination of two or more of the aforementioned insulins.

5. The hepatocyte-targeting composition of claim 1, wherein said lipid component comprises at least one lipid selected from the group consisting of 1,2-distearoyl-sn-glycero-3-phosphocholine, 1,2-dipalmitoyl-sn-glycero-3-phosphocholine, 1,2-dimyristoyl-sn-glycero-3-phosphocholine, cholesterol, cholesterol oleate, dicetylphosphate, 1,2-distearoyl-sn-glycero-3-phosphate, 1,2-dipalmitoyl-sn-glycero-3-phosphate, and 1,2-dimyristoyl-sn-glycero-3-phosphate.

6. The hepatocyte-targeting composition of claim 1, wherein said lipid component comprises a mixture of 1,2-distearoyl-sn-glycero-3-phosphocholine, cholesterol and dicetylphosphate.

7. The hepatocyte-targeting composition of claim 1, wherein said bridging component is chromium.

8. The hepatocyte-targeting composition of claim 1, wherein said complexing component comprises poly(bis)[N-(2,6-diisopropylphenylcarbamoylmethyl)iminodiacetic acid].

9. A method of manufacturing a hepatocyte-targeting composition of claim 1 comprising:

creating a target molecule complex, wherein said complex comprises multiple linked individual units and a supra-molecular lipid construct matrix;

forming a suspension of the target molecule complex in water;

adjusting the pH of said water suspension to approximately pH 5.3;

adjusting the pH of said glargine insulin to approximately 4.8; and combining said glargine insulin, said non-glargine insulin and said target molecule complex.

10. A method of treating a patient for Type I or Type II diabetes comprising administering to the patient an effective amount of a hepatocyte targeted composition of claim 1.

11. The method of treating a patient according to claim 10, wherein the route of administration is selected from the group consisting of oral, parenteral, subcutaneous, pulmonary and buccal.

12. The method of treating a patient according to claim 10, wherein the route of administration is oral or subcutaneous.

13. The method of treating a patient according to claim 10, wherein said nonglargine insulin comprises insulin-like moieties, including fragments of insulin molecules, that have biological activity of insulins.

14. A kit for treating Type I or Type II diabetes in a mammal, said kit comprising the hepatocyte-targeting composition of claim 1, a physiological buffered solution, an applicator, and an instructional material for the use thereof.

* * * * *

SEQUENCE LISTING

```
<160> NUMBER OF SEQ ID NOS: 1

<210> SEQ ID NO 1
<211> LENGTH: 53
<212> TYPE: PRT
<213> ORGANISM: Artificial Sequence
<220> FEATURE:
<223> OTHER INFORMATION: Recombinantly Synthesized Human Glargine
      Insulin Analog

<400> SEQUENCE: 1

Gly Ile Val Glu Glu Cys Cys Thr Ser Ile Cys Ser Leu Tyr Gln Leu
1               5                   10                  15

Glu Asn Tyr Cys Gly Phe Val Asn Gln His Leu Cys Gly Ser His Leu
            20                  25                  30

Val Glu Ala Leu Tyr Leu Val Cys Gly Glu Arg Gly Arg Arg Thr Lys
        35                  40                  45

Pro Thr Tyr Phe Phe
    50
```